United States Patent [19]

Haugwitz et al.

[11] 4,076,827
[45] Feb. 28, 1978

[54] METHOD OF TREATING HELMINTHIASIS BY PARENTERAL ADMINISTRATION OF SULFOXIDE DERIVATIVES OF BENZIMIDAZOLES

[75] Inventors: Rudiger D. Haugwitz, Titusville; Larry R. Cruthers, Flemington, both of N.J.

[73] Assignee: E. R. Squibb & Sons, Inc., Princeton, N.J.

[21] Appl. No.: 791,828

[22] Filed: Apr. 28, 1977

[51] Int. Cl.² ............................... A61K 31/415
[52] U.S. Cl. .................................... 424/273 R
[58] Field of Search .............................. 424/273

[56] References Cited
U.S. PATENT DOCUMENTS

| | | | |
|---|---|---|---|
| 3,574,845 | 4/1971 | Actor et al. | 424/273 |
| 3,928,375 | 12/1975 | Duwel et al. | 260/309.2 |
| 3,954,791 | 5/1976 | Loewe et al. | 424/273 |

Primary Examiner—Sam Rosen
Attorney, Agent, or Firm—Lawrence S. Levinson; Merle J. Smith; Burton Rodney

[57] ABSTRACT

A method is provided for treating or inhibiting helminthiasis by parenterally administering sulfoxide derivatives of benzimidazoles having the structure

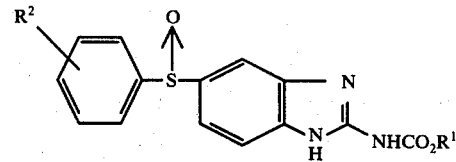

wherein $R^1$ is lower alkyl or phenyl-lower alkyl, and $R^2$ is hydrogen, lower alkyl, halogen, lower alkoxy or nitro. Pharmaceutical compositions for use in the above method are also provided.

8 Claims, No Drawings

METHOD OF TREATING HELMINTHIASIS BY PARENTERAL ADMINISTRATION OF SULFOXIDE DERIVATIVES OF BENZIMIDAZOLES

BACKGROUND OF THE INVENTION

Various benzimidazole compounds are known for their use as anthelmintic agents. For example, U.S. Pat. No. 3,574,845 to Actor et al and assigned to Smith Kline discloses 5(6)-benzene ring substituted benzimidazole-2-carbamate derivatives including 5(6)-methylthio-2-carboethoxyaminobenzimidazole and various 5(6)-alkyl-2-carbomethoxyaminobenzimidazoles.

U.S. Pat. Nos. 3,929,821 and 4,002,640 to Beard et al and assigned to Syntex disclose various 5(6)-benzene ring substituted benzimidazole-2-carbamate derivatives including 5(6)-alkylsulfinyl-2-carbomethoxyaminobenzimidazoles, as well as 5(6)-benzylsulfinyl-2-carbomethoxyaminobenzimidazole, 5(6)-phenylsulfinyl-2-carbomethoxyaminobenzimidazole, 5(6)-cycloalkylsulfinyl-2-carbomethoxyaminobenzimidazoles and 5(6)-cyclopropylmethylsulfinyl-2-carbomethoxyaminobenzimidazole.

The benzimidazoles mentioned above are said to be active orally.

Other benzimidazoles useful as anthelmintic agents are disclosed in U.S. Pat. Nos. 3,929,822, 3,929,823, 3,929,824, 3,935,209, 3,965,113 and 4,005,202 all to Beard et al and assigned to Syntex; U.S. Pat. Nos. 3,682,952 to Actor et al, 3,578,676 and 3,694,455 to Dunn, 3,915,986 and 3,969,526 to Gyurik, all assigned to Smith Kline; and U.S. Pat. No. 3,738,993 to Haugwitz et al assigned to Squibb.

The aforementioned patents teach that the benzimidazole compounds disclosed therein are useful orally in treating helminthiasis.

U.S. Pat. Nos. 3,954,791 to Loewe et al and 3,928,375 to Duwel et al, both assigned to Hoechst disclose 2-carbalkoxy-amino-benzimidazole-5(6)-phenyl and phenylthio ethers which are said to be active perorally and subcutaneously.

In accordance with the present invention, it is indeed surprising that 5(6)-phenylsulfinyl-2-carbomethoxyaminobenzimidazoles may be effectively administered parenterally in the treatment or prevention of helminthiasis inasmuch as most benzimidazole compounds are active only upon oral administration.

DESCRIPTION OF THE INVENTION

The present invention relates to a method for treating or inhibiting helminthiasis by parenterally administering to a mammalian host a sulfoxide derivative of a benzimidazole having the structure

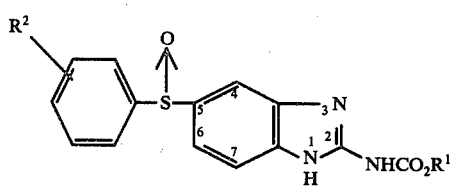

wherein $R^1$ is lower alkyl or phenyl-lower alkyl, and $R^2$ is hydrogen, lower alkyl, lower alkoxy, halogen or nitro.

The term "lower alkyl" as used herein includes straight or branched chain aliphatic hydrocarbon radicals having up to and including seven carbon atoms, such as methyl, ethyl, propyl, isopropyl, n-butyl, isobutyl, t-butyl, amyl, hexyl, heptyl and the like.

The term "lower alkoxy" as used herein refers to lower lower alkyl groups as defined above attached to an oxygen atom.

The term "halogen" as employed herein refers to chlorine, bromine, iodine or fluorine with chlorine and bromine being preferred.

Preferred are those compounds wherein $R^1$ is methyl, ethyl, propyl or benzyl, and $R^2$ is hydrogen.

Examples of compounds which may be employed in the method of the present invention include the following.

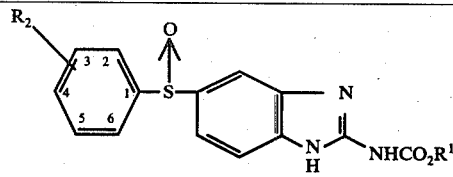

| | $R^1$ | $R^2$ |
|---|---|---|
| 1. | $CH_3$ | H |
| 2. | $CH_3$ | H |
| 3. | $C_2H_5$ | $CH_3$ (4) |
| 4. | $C_3H_7$ | H |
| 5. | $CH_3$ | $NO_2$ (3) |
| 6. | $C_6H_5CH_2$ | H |
| 7. | $C_6H_5CH_2$ | H |
| 8. | $CH_3$ | $C_2H_5O$ (2) |
| 9. | $CH_3$ | Cl (4) |
| 10. | $C_2H_5$ | H |

The benzimidazole derivatives of structure I may be prepared as described in U.S. Pat. Nos. 3,929,821 and 4,002,640 to Beard et al.

In certain instances, the compounds of formula I form physiologically acceptable acid-addition salts with inorganic and organic acids. These salts frequently provide useful means for isolating the products from reaction mixtures by forming the salt in a medium in which it is insoluble. The free base may then be obtained by neutralization. Then any other salt may again be formed from the free base and the appropriate inorganic acid. Illustrative are the hydrohalides, especially the hydrochloride and hydrobromide which are preferred, sulfate, nitrate, tartrate, methanesulfonate, benzenesulfonate, toluenesulfonate, and the like.

In accordance with the present invention, the compounds of formula I are administered parenterally, such as subcutaneously, intravenously, intramuscularly or interperitoneally to a mammalian host in the treatment and/or prevention of helminthiasis. Helminthiasis is a parasitic disease which causes widespread and often serious infection in domesticated animals such as swine, horses, cattle, dogs, cats and sheep. The compounds administered parenterally are useful in treating infections caused by Haemonchus, Ostertagia, Trichostrongylus, Cooperia, Dictyocaulus, Nematodirus, Bunostomum, Strongyloides, Oesophogostomum, Trichuris, and liver flukes. In preparing injectable compositions, the compounds are mixed with a non-toxic, physiologically acceptable non-pyrogenic carrier such as sterile water, sterile saline solution, benzyl benzoate, 1,3-butylene glycol, ethyl oleate, castor oil, glyceryl triacetate, sesame oil, and sesame oil:benzyl benzoate (1:1). The parenteral product will usually take the form of a suspension containing from about 1 to about 10% by weight of the compound of formula I.

The above injectable compositions may also include a non-toxic physiologically acceptable non-pyrogenic suspending agent. Thus, where a non-oily carrier is employed such as water, suspending agents such as carboxymethyl cellulose, methyl cellulose, polyvinyl pyrrolidone or non-antigenic gelatin may be employed. Where the carrier employed is an oil, aluminum monostearate may be employed as a suspending agent. The suspending agent may be employed in amounts ranging from about 0.05 to about 2%, and preferably from about 0.1 to about 1% by volume of carrier (the above % may be based on the weight of the carrier where the carrier is qs to 100g).

A non-toxic, non-pyrogenic wetting agent may also be included in the injectable compositions in amounts ranging from about 0.005 to about 0.2% and preferably from about 0.01 to about 0.1% by weight of the carrier. Examples of suitable wetting agents include non-ionic surfactants such as polyoxyethylene sorbitan monostearate, polyoxyethylene sorbitan monooleate [e.g., (Tweens)] and fatty acid monoglycerides or diglycerides. Other surfactants suitable for use herein are disclosed in the published literature, for example, Kirk-Othmer, Encyclopedia of Chemical Technology, Second Edition, Volume 19, page 507 et seq.

In general, in carrying out the method of the invention, the parenteral composition described above will be administered to animals to a single dose to provide from about 1 to about 100 mg active compound per kilogram of animal body weight. It is preferred to employ in the range of 2.5–25 mg per kilogram of body weight. The compounds may be divided into a plurality of smaller doses given over one or more days, for example, up to 14 days.

The following examples are provided for illustrative purposes and may include particular features of the invention, however the examples should not be construed as limiting the invention, many variations of which are possible without departing from the spirit or scope thereof. All temperatures are in degrees centigrade.

EXAMPLE 1

Parenteral Composition Containing [5-(Phenylsulfinyl)-1H-benzimidazole-2-yl]carbamic acid, methyl ester A. [5-(Phenylsulfinyl)-1H-benzimidazol-2-yl]-carbamic acid, methyl ester To a solution of 4.0 g. of [5-(phenylthio)-1H-benzimidazol-2-yl]carbamic acid, (prepared as described in U.S. Pat. No. 3,965,113) in 120 ml of chloroform acid and 120 ml of acetic acid, there is added a solution of 2.8 g of m-chloroperoxybenzoic acid (85%) in 20 ml of chloroform at 0° C. The reaction mixture is stirred for 3 hours allowing it to warm to room temperature. The solvent is removed in vacuo and the residue is neutralized with aqueous NaHCO$_3$. The resulting solid is filtered off and crystallized from glyme to yield 2.4 g of product, m.p. ~250°, resolidifies, remelts 285°–286° C. Lit m.p. ~250° C. resolidifies, remelts 275°–278° C. J. Med Chem 18, 1164 (1975).

B. Parenteral Formulation of [5-(phenylsulfinyl)-1H-benzimidazol-2-yl]carbamic acid, methyl ester A suspension suitable for subcutaneous administration is prepared by dispersing 150 mg of [5-(phenylsulfinyl)-1H-benzimidazole-2-yl]carbamic acid, methyl ester in about 10 ml of water for injection, USP. The resulting suspension contains 1.5% by weight of the benzimidazole compound.

EXAMPLE 2

Testing of Parenteral Formulation of [5(Phenylsulfinyl)-1H-benzimidazol-2yl]carbamic acid, methyl ester The following test is carried out to determine the effectiveness of treating sheep infected with gastrointestinal nematodes by subcutaneously administering a single dose of an aqueous suspension of [5-(phenylsulfinyl)-1H-benzimidazol-2yl]carbamic acid, methyl ester (hereinafter referred to as "benzimidazole compound") prepared in Example 1 so as to inject 10 mg of the "benzimidazole compound" per kg of body weight of the test animal.

Egg per gram of feces (EPG) counts are conducted 2–4 days (avg. 3) prior to subcutaneously administering the "benzimidazole compound" in order to determine the degree of parasitism of the test animal. Generally, animals are used which have at least 10,000 eggs per gram of feces although, on occasion, lambs with 8–9,000 eggs per gram can be used. An average pretreatment EPG is calculated for the test animal and medication is given according to individual body weight (10 mg/kg).

EPG's are conducted daily during the week the animal is on test and the final three (3) EPG's are used to calculate an average post-treatment EPG. The percent reduction in the EPG count for a given compound is calculated by taking the average pretreatment EPG and dividing this figure into the average post-treatment EPG and subtracting the quotient from 100.

The "benzimidazole compound" in the form of an aqueous suspension reduces the fecal egg count (EPG) by 87% in one sheep and by 57% in a second sheep when administered subcutaneously at 10 mg/kg.

What is claimed is:

1. A method of treating or preventing helminthiasis, which comprises parenterally administering to a mammalian host an effective amount of a compound of the structure

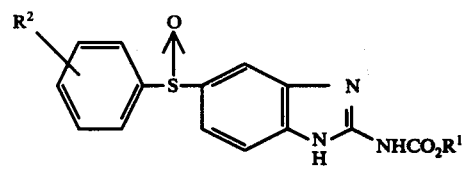

wherein R$^1$ is lower alkyl or phenyl-lower alkyl, R$^2$ is hydrogen, lower alkyl, lower alkoxy, halogen or nitro dispersed in a non-toxic non-pyrogenic physiologically acceptable carrier.

2. The method as defined in claim 1 where in said compound R$^1$ is lower alkyl or benzyl.

3. The method as defined in claim 1 where in said compound R$^2$ is hydrogen.

4. The method as defined in claim 1 wherein said compound has the name [5-(phenylsulfinyl)-1H-benzimidazol-2-yl]carbamic acid, methyl ester.

5. The method as defined in claim 1 wherein said compound is administered subcutaneously.

6. The method as defined in claim 1 wherein said compound is administered intravenously.

7. An injectable composition for use in treating or preventing helminthiasis in mammalian species comprising an effective amount of a compound of the structure

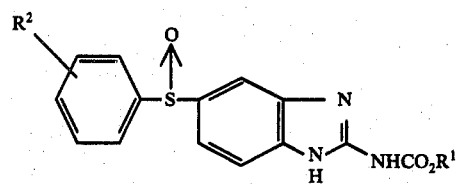

wherein $R^1$ is lower alkyl or phenyl-lower alkyl, $R^2$ is hydrogen, lower alkyl, lower alkoxy, halogen or nitro, and a non-toxic non-pyrogenic physiologically acceptable carrier therefor selected from the group consisting of sterile water for injection, benzyl benzoate, 1,3-butylene glycol, ethyl oleate, glyceryl triacetate, mixtures thereof and a mixture of benzyl benzoate and sesame oil.

8. The composition as defined in claim 7 wherein said compound has the name [5-(phenylsulfinyl)-1H-benzimidazol-2-yl]carbamic acid, methyl ester.

* * * * *